United States Patent [19]

Francese et al.

[11] Patent Number: 5,553,624
[45] Date of Patent: Sep. 10, 1996

[54] ENDOSCOPIC BIOPSY FORCEPS JAWS AND INSTRUMENTS INCORPORATING SAME

[75] Inventors: Jose L. Francese, Miami Springs; John R. Whittier, Miami, both of Fla.

[73] Assignee: Symbiosis Corporation, Miami, Fla.

[21] Appl. No.: 310,857

[22] Filed: Sep. 22, 1994

Related U.S. Application Data

[63] Continuation-in-part of Ser. No. 177,536, Jan. 5, 1994, Pat. No. 5,394,885, and a continuation-in-part of Ser. No. 256,217, Jun. 23, 1994, which is a continuation of Ser. No. 16,595, Feb. 11, 1993, abandoned.

[51] Int. Cl.$^6$ .................................................... A61B 17/28
[52] U.S. Cl. ............................................ 128/751; 606/207
[58] Field of Search .............................. 606/51, 53, 170, 606/174, 205–211; 128/750–755; 254/99.1; 81/419, 424.5

[56] References Cited

U.S. PATENT DOCUMENTS

| | | |
|---|---|---|
| 825,829 | 7/1906 | Heath . |
| 3,515,135 | 6/1970 | Mallina ................................... 606/207 |
| 3,608,554 | 9/1971 | McGuinness et al. ................... 606/207 |
| 3,895,636 | 7/1975 | Schmidt . |
| 4,880,015 | 11/1989 | Nierman . |
| 5,059,214 | 10/1991 | Akopov et al. . |
| 5,228,451 | 7/1993 | Bales et al. . |
| 5,304,203 | 4/1994 | El-Mallawany et al. ............... 128/751 |

*Primary Examiner*—Gary Jackson
*Assistant Examiner*—William Lewis
*Attorney, Agent, or Firm*—David P. Gordon

[57] ABSTRACT

Endoscopic biopsy forceps jaws having an outer edge which may be generally U-shaped, circular, or oblate circular are disclosed with a number of teeth which extend along at least a portion of the outer edge where the peaks of the teeth are located upward and inward from the outer edge. In one embodiment, each tooth is defined by a substantially triangular inner surface, a substantially quadrilateral base, and a surface which extends outward and downward from the vertex of the triangular surface to the outer edge of the jaw. Valleys between the teeth have two inclined surfaces which intersect along a line which extends inward and downward from the outer edge of the jaw. In a second embodiment, the peak of each tooth is defined by the vertex of a pyramid having four faces and valleys between these teeth have three substantially flat surfaces which intersect at a vertex which lies downward and inward from the outer edge of the jaw. Alternate embodiments of both the first and second embodiment of the jaws include providing a lip around the outer portion of the outer edge so that the teeth and valleys are spaced farther in from the outer surface of the jaw cup.

22 Claims, 13 Drawing Sheets

ENDOSCOPIC BIOPSY FORCEPS JAWS AND INSTRUMENTS INCORPORATING SAME

This application is a continuation-in-part of co-owned application Ser. No. 08/177,536 filed Jan. 5, 1994, now U.S. Pat. No. 5,394,885 and of co-owned Ser. No. 08/265,217 filed Jun. 23, 1994 which in turn is a continuation of now abandoned Ser. No. 08/016,595 filed Feb. 11, 1993.

BACKGROUND OF THE INVENTION

1. Field of the Invention

The present invention relates to endoscopic biopsy forceps devices. In particular, the invention relates to biopsy forceps jaws having radially inclined teeth and biopsy forceps jaws having teeth which extend completely around the outer edge of a biopsy forceps jaw cup.

2. State of the Art

Endoscopic biopsy forceps are used for taking tissue samples from the human body for analysis. These forceps typically have a pair of cupped jaws attached to the distal end of a long flexible coil, the proximal end of which is attached to actuating means which opens and closes the jaws when the actuating means is manipulated by the practitioner. The endoscopic biopsy procedure is accomplished through an endoscope which is inserted into a body and guided by manipulation to the biopsy site. The endoscope typically includes a long narrow flexible tube carrying distal optical means and having a narrow lumen for receiving the biopsy forceps. The practitioner guides the endoscope to the biopsy site using the optical means and inserts the forceps, with jaws closed, through the lumen of the endoscope to the biopsy site. While viewing the biopsy site through the optical means of the endoscope, the practitioner opens the forceps jaws and carefully guides the jaws around a tissue to be sampled. When the jaws are in the correct position, the practitioner manipulates the actuating means and closes the jaws on the tissue to be sampled. The cupped jaws grip the tissue and enclose a sample of the tissue in the space between the cupped jaws. The forceps are then withdrawn from the lumen of the endoscope while the jaws are kept shut, with the sample captured in the space between the cupped jaws typically torn away from the tissue at the biopsy site.

The endoscopic biopsy procedure poses several challenges to the design and manufacture of biopsy forceps and particularly biopsy forceps jaws. The jaws must be small enough to fit through the narrow lumen of the endoscope, yet strong enough and sharp enough to cut and/or tear tissue. An early example of an endoscopic biopsy forceps is shown in U.S. Pat. No. 3,895,636 to Schmidt. The forceps in Schmidt include a pair of cupped toothless jaws with sharpened opposed edges intended to cut through tissue being sampled. Due to the miniature size of the jaws, however, it is difficult to sharpen the edges to a very high degree. Consequently, it is necessary to apply great force to the jaws in order to sever the tissue being sampled. In practice, sufficient force to sever the tissue is rarely achieved. Thus, either the jaws effect a clamping action which permits the tissue to be torn away from the biopsy site, or the jaws simply slip off the tissue without cutting or tearing it.

U.S. Pat. No. 4,880,015 to Nierman shows endoscopic biopsy forceps having opposed rectangularly cupped jaws with teeth on their parallel edges. When the jaws close, opposed teeth interleave providing a slightly better gripping ability than the jaws disclosed by Schmidt. However, the rectangular configuration of the jaws and the absence of teeth at the distal end of the jaws limits their functionality. Additionally, with these jaws and other toothed jaws, the teeth often do not align properly and prevent the jaws from closing completely which adds to the inefficiency of cutting and/or tearing. Similarly, the misalignment of the opposed teeth sometimes causes the jaws to lock in the closed position.

Co-owned U.S. Pat. No. 5,228,451 to Bales et al., the complete disclosure of which is hereby incorporated by reference herein, discloses endoscopic biopsy forceps having a pair of opposed jaws with teeth which extend along the entire U-shaped outer edge of each jaw. The teeth are offset by one-half pitch relative to the longitudinal center line of the jaw so that the upper jaw and lower jaw can be made from the same mold and still allow the teeth to align (interleave) when the jaws are closed. This arrangement of jaw teeth greatly improves the cutting and/or gripping (tearing) action of the forceps. It is a perceived problem, however, that this arrangement of teeth may expose a rough outer surface even when the jaws are closed during their entry into and exit from the lumen of the endoscope. It is believed by some that the perceived rough outer surface of the closed jaws might cause damage or undue wear to the lumen of the endoscope.

Parent application Ser. No. 08/177,436, discloses biopsy forceps jaws where the cup of each jaw has a wall with an outer side portion having a cup edge and an inner side portion in which teeth are formed. The teeth are defined by peaks and valleys formed in the inner side portion of the wall of the cup such that the peaks of the teeth rise above the edge and the valleys remain below the edge of the outer side portion of the cup wall. In order to form the teeth in the inner side portion of the wall, the radial thickness of the teeth is less than the radial thickness of the cup wall, thereby causing the radially outer surface of the teeth to be spaced radially inward from the outer surface of the cup wall. When the two opposed jaws close, the peaks of the teeth on one jaw enter the valleys of the teeth on the other jaw and the edges of the cup walls of the two jaws touch. In the closed position, the teeth of the two jaws are enclosed by the cup walls and the outer surface of the closed jaws is smooth. The cups of the jaws are provided with the general shape of an oblate hemisphere or a portion of an oblate hemisphere, and the teeth are radially arranged around at least a portion of the periphery of the cup and are offset by one half pitch relative to the longitudinal center line of the cup so that two opposed identical jaws will mate as described in co-owned U.S. Pat. No. 5,228,451 to Bales et al. In addition, the radially outer surface of the peaks and the radially inner surface of the valleys are radially chamfered. Thus, as the radially chamfered peaks of the teeth of one jaw enter the radially chamfered valleys of the teeth of the other jaw, moving points of contact between the outer edges of the peaks and the cup wall edge above the valleys cause a scissoring action when the jaws are near fully closed. The radial chamfering also aids in preventing the jaws from jamming should they become misaligned to a point where the peak of a tooth on one jaw might stop against the cup wall of a mating jaw.

Parent application Ser. No. 08/265,217, discloses endoscopic biopsy forceps having selective bipolar cautery in which a variety of different types of forceps jaws are shown including jaws having teeth which extend completely around an oblate circular outer edge of the jaw cup.

SUMMARY OF THE INVENTION

It is therefore an object of the invention to provide endoscopic biopsy forceps jaws, wherein each one of a mating pair of jaws are identical to each other.

It is also an object of the invention to provide endoscopic biopsy forceps jaws which are self-aligning and which permit greater tolerance in the dimensions of the jaws during manufacture.

It is another object of the invention to provide toothed endoscopic biopsy forceps jaws which present a smooth outer surface when closed.

It is an additional object of the invention to provide toothed endoscopic biopsy forceps jaws having superior cutting and/or tearing ability.

A further object of the invention is to provide endoscopic biopsy forceps jaws having teeth which align to allow the jaws to close completely without locking.

Another object of the invention is to provide endoscopic biopsy forceps jaws having teeth which are radially inclined.

An additional object of the invention is to provide endoscopic biopsy forceps jaws having teeth which are radially arranged around the outer edge of the jaw and offset by one half pitch relative to the longitudinal center line of the jaw.

Yet another object of the invention is to provide endoscopic biopsy forceps jaws having teeth which extend completely around the outer edge of the jaw.

It is even a further object of the invention to provide an endoscopic biopsy forceps instrument which incorporates the jaws of the invention.

In accord with these objects which will be discussed in detail below, the endoscopic biopsy forceps jaws of the present invention are generally hemispherically shaped cups having an outer edge which may be generally U-shaped, circular, or oblate circular with the distal portion of the edge being curved. In a preferred embodiment, a number of teeth are arranged radially (circumferentially) along at least a portion of the outer edge including the curved distal portion. Pairs of adjacent teeth on each jaw may be said to define interposed valleys within which teeth from the opposing jaw mesh. In order that a pair of cooperating jaws may be made from a single mold, the teeth are offset by one half pitch relative to the longitudinal center line of the jaw as described in co-owned U.S. Pat. No. 5,228,451 to Bales et al.

According to one embodiment of the jaws, each tooth is defined by a portion of the outer edge, an inner triangular surface with a vertex, an inclined line running down from the vertex of the inner surface out to a midpoint of the portion of the outer edge, and two preferably straight side lines at the same height as the outer edge. The valleys between these teeth are similarly defined by a portion of the outer edge between tooth portions, an inner triangular opening with a nadir, an inclined line running up from the nadir to a midpoint on the portion of the outer edge, and two side lines shared with adjacent teeth. In this embodiment, all of the teeth are thereby inclined upward and inward from the outer edge of the jaw cup, while the valleys are inclined inward and downward from the outer edge of the jaw cup. When two cooperating jaws close, the teeth of one jaw enter the valleys of the other jaw. When closed, the outer surface of the jaws is substantially smooth and shows only as a straight line interface between the outer edges of the opposed jaws, while the inside surface of the jaws looks like triangular teeth meshing with triangular valleys.

According to a second embodiment of the jaws, each tooth is a four faced pyramid with the peak of each tooth being defined by the vertex of the pyramid. The valleys between these teeth have three substantially flat surfaces which intersect at a nadir which lies downward and inward from the outer edge of the jaw. All of the teeth are inclined inward and upward from the outer edge of the jaw cup and the valleys are inclined inward and downward from the outer edge of the cup. When two cooperating jaws close and the teeth of one jaw enter the valleys of the other jaw, the outer surface of the jaws is substantially smooth and shows only as a straight line interface between the outer edges of the opposed jaws, while the inside surface of the jaws looks like triangular teeth meshing with triangular valleys.

Alternate embodiments of both the first and second embodiment of the jaws include providing a lip around the outer portion of the outer edge so that the teeth and valleys are spaced farther in from the outer surface of the jaw cup. The lip may be sharp or dull. The tooth geometry of either the first or second embodiment can be utilized in jaw cups having an outer edge which is U-shaped, circular, or oblate circular. Where the jaw cups are circular or oblate circular, the teeth may be arranged so that they extend completely around the edge of the jaw. Further combinations and permutations of the features of the different embodiments will be apparent from the detailed description below.

The present invention also provides an endoscopic biopsy forceps instrument which generally includes a flexible coil having a proximal and a distal end, at least one pull wire extending through the coil, an actuation handle coupled to the proximal ends of the coil and the pull wire(s), and a clevis coupled to the distal end of the coil. Each of the embodiments of the endoscopic biopsy forceps jaws is provided with a proximal tang having means for rotatably mounting to the clevis and a means for coupling the tang to the distal end of a pull wire. Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
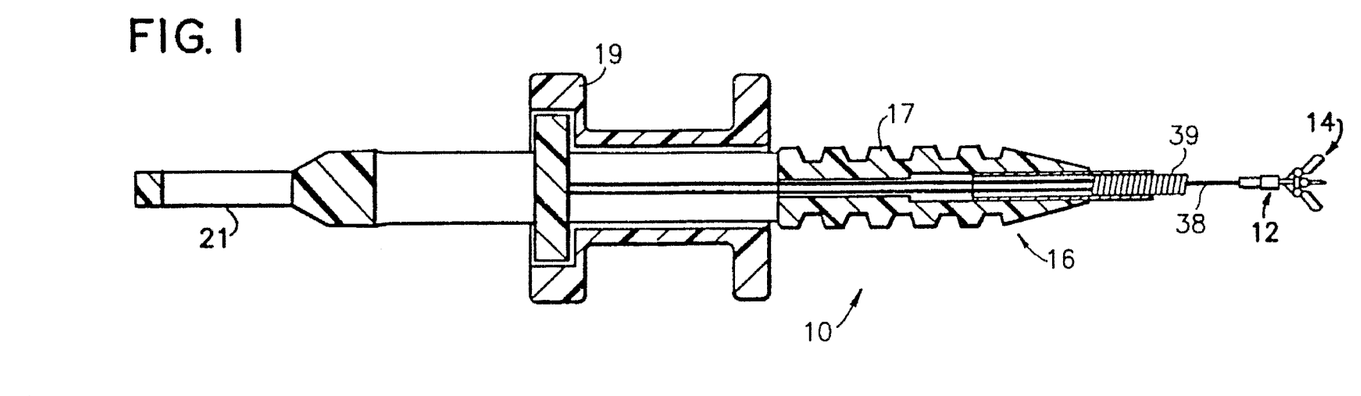
FIG. 1 is a side elevation view, partially in cross-section of a preferred endoscopic biopsy forceps instrument according to the invention.
Figure 2:
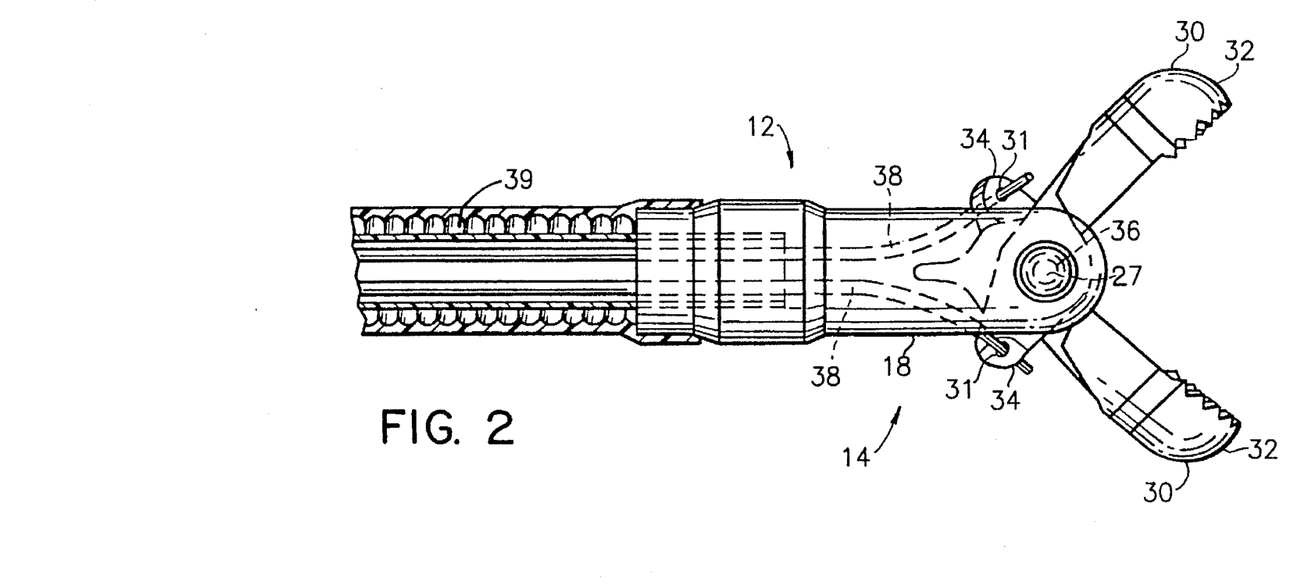
FIG. 2 is an enlarged side elevation view of the distal end of the biopsy forceps instrument of FIG. 1 with a first embodiment of biopsy forceps jaws according to the invention.

Referring now to FIGS. 1 and 2, the preferred endoscopic biopsy forceps instrument 10 of the invention is shown with a distal end 12 having a biopsy jaw assembly 14, and a proximal end 16 having a handle 17, a spool 19 and a thumb ring 21. The biopsy jaw assembly 14 generally includes a clevis 18 and a pair of identical jaws 30. Each identical jaw 30 has a distal toothed cup 32, a proximal tang 34, and a transverse mounting bore 36. The jaws 30 are mounted on the clevis 18 by a pin 37 which passes through their mounting bores 36. The proximal tang 34 of each jaw is provided with a pull wire coupling bore 31 and is thereby coupled to the distal end of a control member or pull wire 38 which extends through a hollow member or coil 39. The proximal end of each pull wire 38 is coupled to the spool 19 which is slidably attached to the handle 17. The jaws are opened and closed by movement of the spool 19 relative to the handle 17 as described more fully in co-owned U.S. Pat. No. 5,228,451 to Bales et al.

FIGS. 3, 3a–3e, and 4 through 8 show a first embodiment of the biopsy forceps jaws 30. In the first embodiment, the distal toothed cup 32 of the jaw 30 is an oblate hemispherical member having a generally U-shaped outer edge 33, a hollow interior 35, and an optional fenestration hole 37 at the bottom of the hollow interior 35. Extending from the outer edge 33 are a number of teeth 40–51 which are separated by a corresponding number of valleys 40V–51V. As seen best in FIG. 3, the curved distal end of the cup 32 is provided with teeth 43–48 and valleys 43V–48V at least some of which are radially arranged about a point "R" as described more fully in co-owned U.S. Pat. No. 5,228,451 to Bales et al. Additionally, in the preferred embodiment, the teeth 40–42 and the valleys 40V–42V on one side of the longitudinal centerline "CL" of the cup 32 are displaced by one half pitch from the teeth 49–51 and the valleys 49V–51V on the other side of the centerline of the cup 32. This radial arrangement and half pitch displacement provides for self-alignment and the ability to use a single cast to make a pair of identical mating jaws as described in U.S. Pat. No. 5,228,451 to Bales et al. Since the teeth do not completely encircle the cup 32, parting line planes 40p and 51p are provided proximal of valley 40v and tooth 51, respectively According to the first embodiment of the invention, and as seen best in FIGS. 3a–3d, each tooth rises as it extends inward from the outer edge 33 to a triangular face T on the inner surface 33a of the jaw cup 32. The base of each tooth can be described as a quadrilateral having sides L1–L4. Side L1 is a portion of the outer edge 33 of the cup 32. Sides L2 and L3 are imaginary lines which extend inward from the outer edge 33 at the same elevation as the outer edge 33. Side L4 is an imaginary line which connects lines L2 and L3 and is the base of the triangular face T. A tooth edge E extends outward and downward from the vertex V of the triangular face T to the midpoint of side L1. Those skilled in the art will appreciate that the surfaces S1 and S2 formed between the edge E and the sides L2 and L3 are relatively complex, but may be approximately described as trapezoidal planes which have been twisted to a peak V. The twisted trapezoidal plane may be understood by appreciating that the distance between point P1 (intersection of L1 and L3) and point P2 (intersection of L1 and E) is smaller than the distance between point P3 (intersection of L3 and L4), and point V. Thus, if P1, P2, P3, and V were in the same plane, with lines L1 and L7 being parallel, they would form a trapezoid. However, while all of the points along lines L1, L2, and L3, including P1, P2, and P3 preferably lie in the same horizontal plane, point V lies in a different plane. Thus, the trapezoid is twisted.

To further define the surfaces S1 and S2, it should be appreciated that in the preferred embodiment, lines L2, L3, and edge E (when projected into the horizontal plane) are all preferably parallel to each other; and the distance between E and L2 or L3 increases as the peak of the tooth rises. The surfaces S1 and S2, therefore, are not completely planar (flat). Depending on how the jaw cup is made, the geometrical conditions set forth above may be satisfied by surfaces S1 and S2 which are concave, convex, or a combination of concave and convex. Moreover, the surfaces S1 and S2 may be formed from a series of faceted surfaces where each facet is a slightly twisted trapezoid. Each facet could also be formed as two planar triangles in order to facilitate machining. The twisted trapezoids may take either a convex or concave form, or may alternate between convex or concave in order to form as flat a surface as possible. It should be appreciated that whether edge E is a straight line or a curved line will influence the surface geometry of surfaces S1 and S2. Likewise, it will be appreciated that edge E does not have to be a discontinuity between surfaces S1 and S2, but may rather be a line of highest topology which artificially separates surfaces S1 and S2.

Interposed between each tooth is a valley which has a geometry for receiving an opposed tooth. In particular, each valley descends from the outer edge 33 of the cup 32 to a triangular opening T0 in the inner surface 33a of the cup 32. The base of each valley can be described as a quadrilateral having sides L5, L2, L3, and L6. Side L5 is a portion of the outer edge 33 of the cup 32. Sides L2 and L3 are the imaginary lines described above from teeth adjacent to the valley. Side L6 is an imaginary line colinear with the imaginary lines L4 from adjacent teeth. A valley trough VT extends upward from the nadir N of triangular opening T0 to the midpoint of L5. The surfaces S3 and S4 formed between the valley trough VT and the imaginary lines L2 and L3 have a geometry which preferably is the inverse of the geometry of the surfaces S1 and S2 on the teeth. In this way, each valley will mesh with an opposing tooth without any significant gap between mating surfaces. However, if desired, surfaces S3 and S4, rather than having an inverse geometry to those of surfaces S1 and S2 can have an identical geometry thereto, particularly, if the geometry is generally concave. With such an arrangement, gaps would be generated between the teeth and valleys of the opposing jaws.

Those skilled in the art will appreciate that the imaginary line L2 need not be a discontinuity between surfaces S1 and S4 and that these two surfaces may be seen as a single continuous surface extending from an edge E to an adjacent valley trough VT. Such a continuous surface may be approximately described as a twisted trapezoidal plane. The same is true for line L3, and surfaces S2 and S3.

Figure 3:
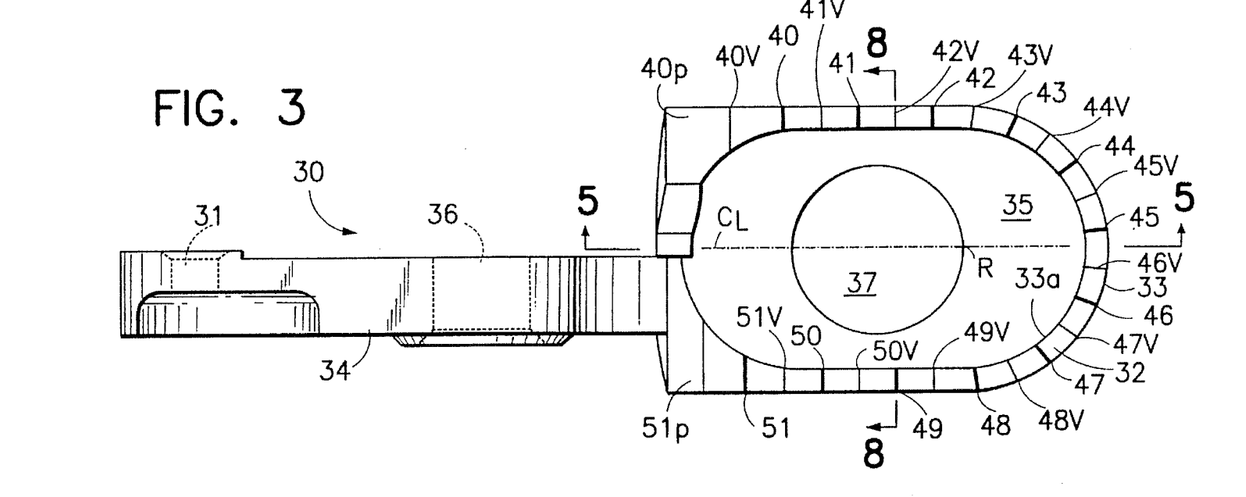
FIG. 3 is a top view of one of the jaws of FIG. 2.
Figure 3A:
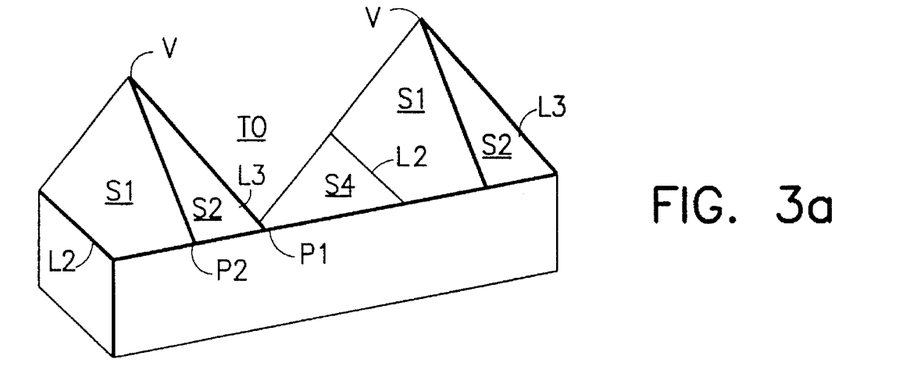
FIGS. 3a–3c are partial perspective views of several teeth and valleys of the jaw of FIG. 3.
Figure 3B:
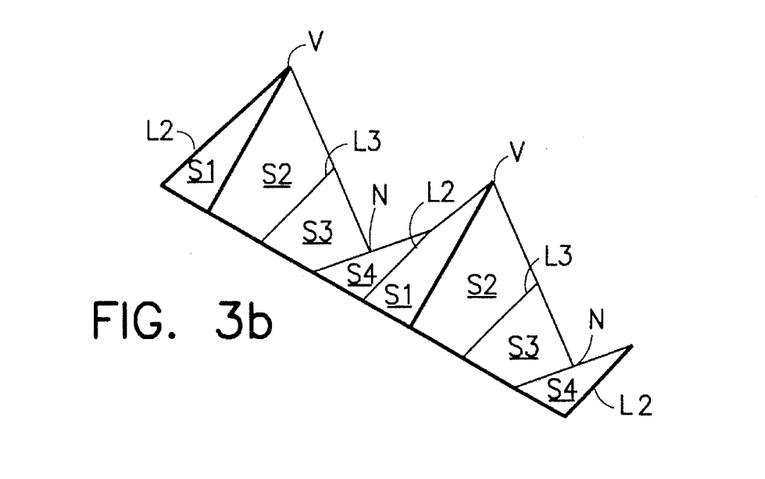
Figure 3C:
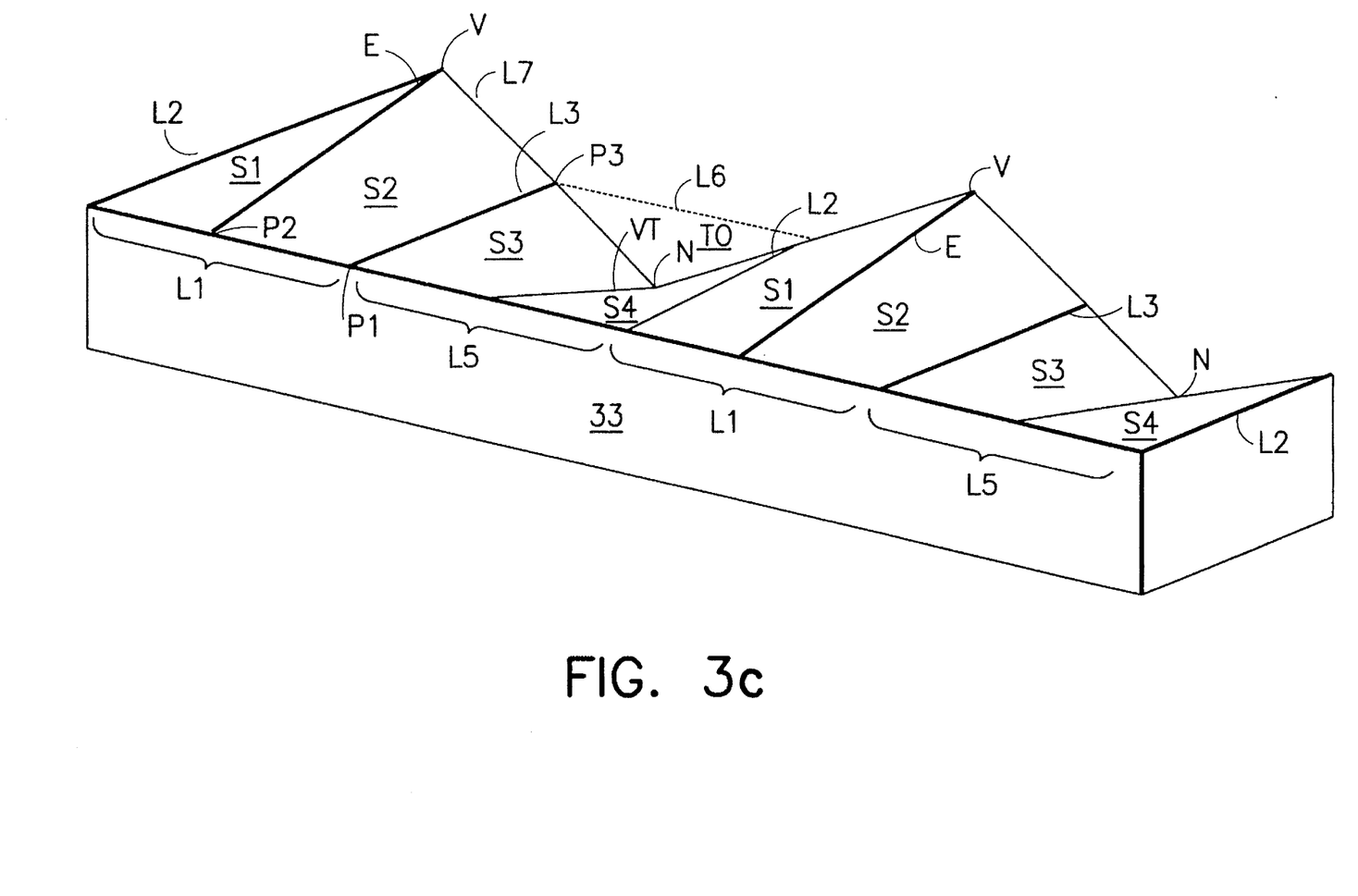
Figure 3D:
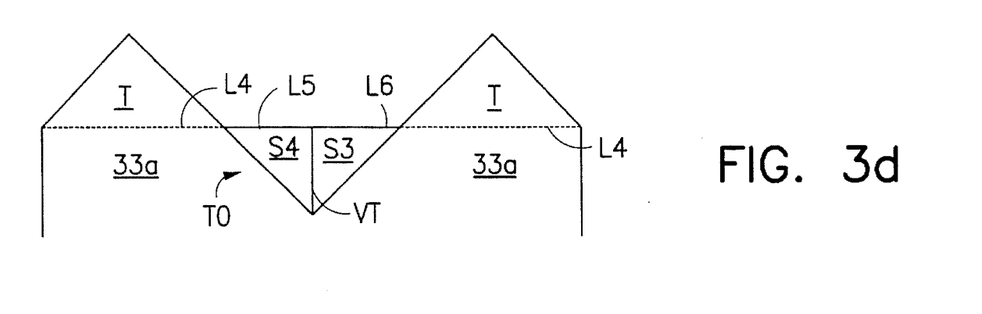
FIG. 3d is a broken side elevational view showing two teeth and one valley of the jaw of FIG. 3 as viewed from inside the jaw.
Figure 3E:
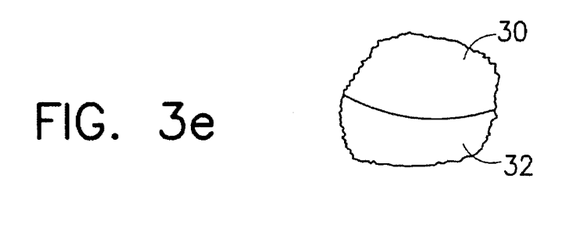
FIG. 3e is a broken perspective view of portions of two biopsy forceps jaws of the embodiment of FIG. 3 in the closed position.
Figure 4:
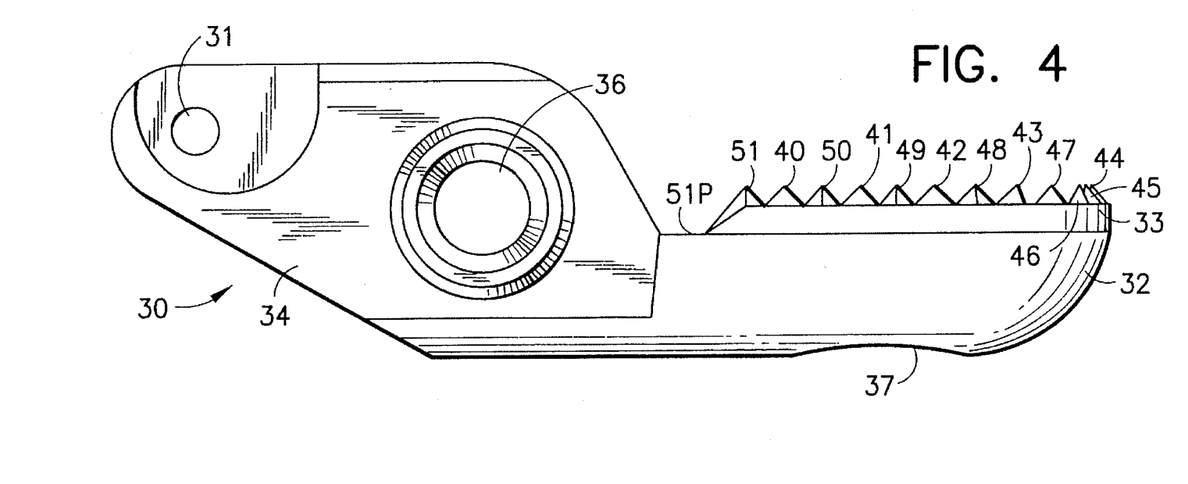
FIG. 4 is a side elevation view of the jaw of FIG. 3.
Figure 5:
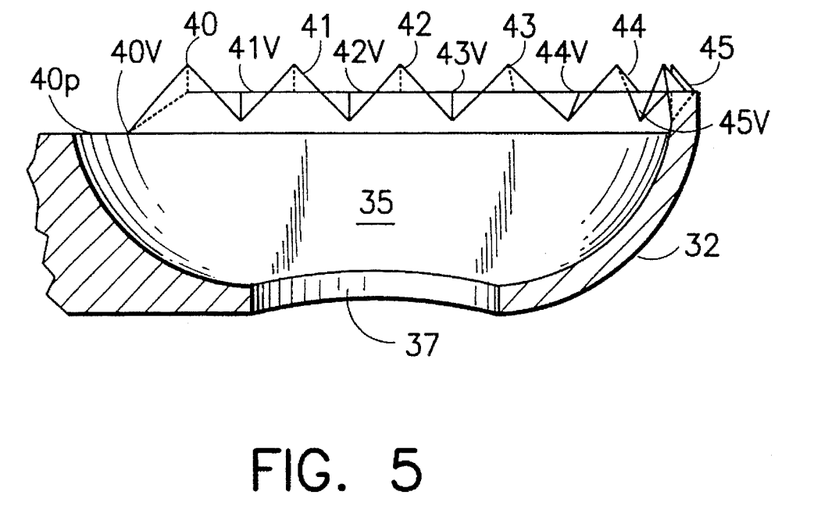
FIG. 5 is a cross sectional view along line 5—5 of FIG. 3.
Figure 6:
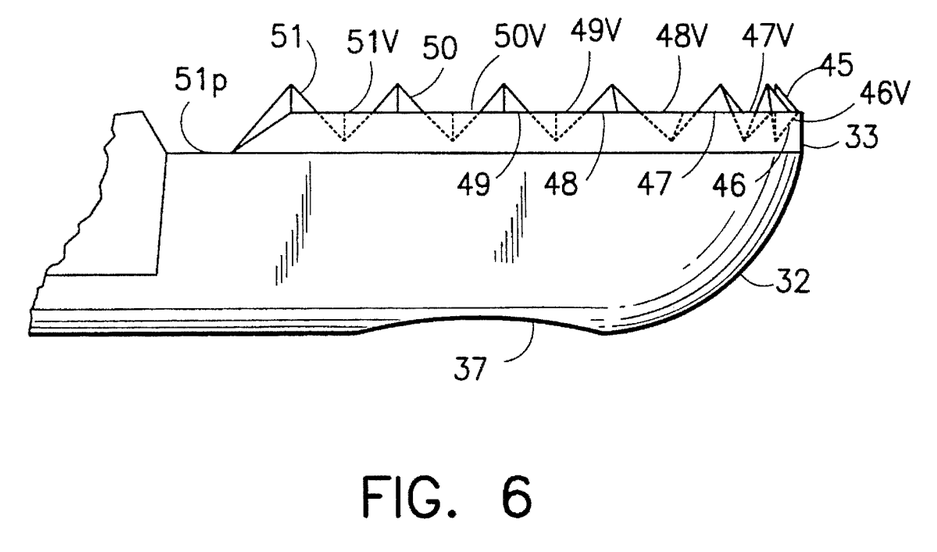
FIG. 6 is a broken side elevation view of a portion of the jaw of FIG. 3.
Figure 7:
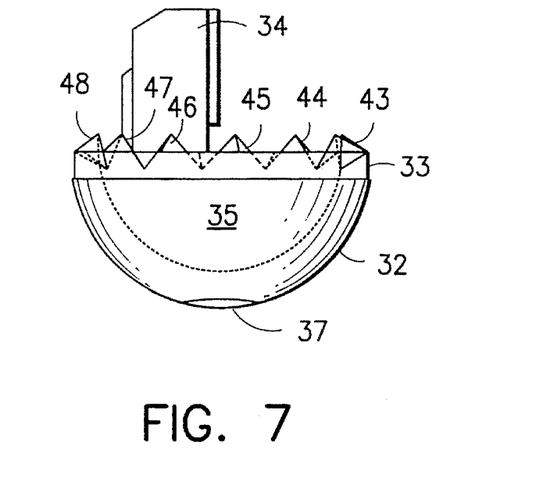
FIG. 7 is a distal end view of the jaw of FIG. 4.
Figure 8:
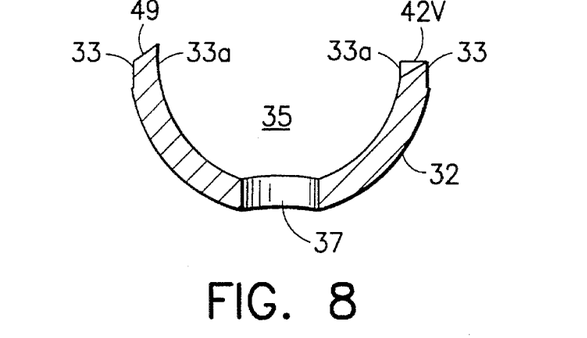
FIG. 8 is a partial sectional view along line 8—8 in FIG. 3.

While the surface structure of the first embodiment of the invention is somewhat complex, it will be appreciated that the top view of the teeth has virtually the same appearance as the top view of the teeth of the parent application Ser. No. 08/265,217 which have two triangular faces and two rectangular faces (see also FIGS. 14–17, and 19 herein below). Moreover, as seen in FIG. 3e, when the jaws are closed, they present a smooth outer surface with a straight line interface between outer edges, while from the inside (see FIG. 3d), they present triangular teeth meshed with triangular valleys.

Figure 9:
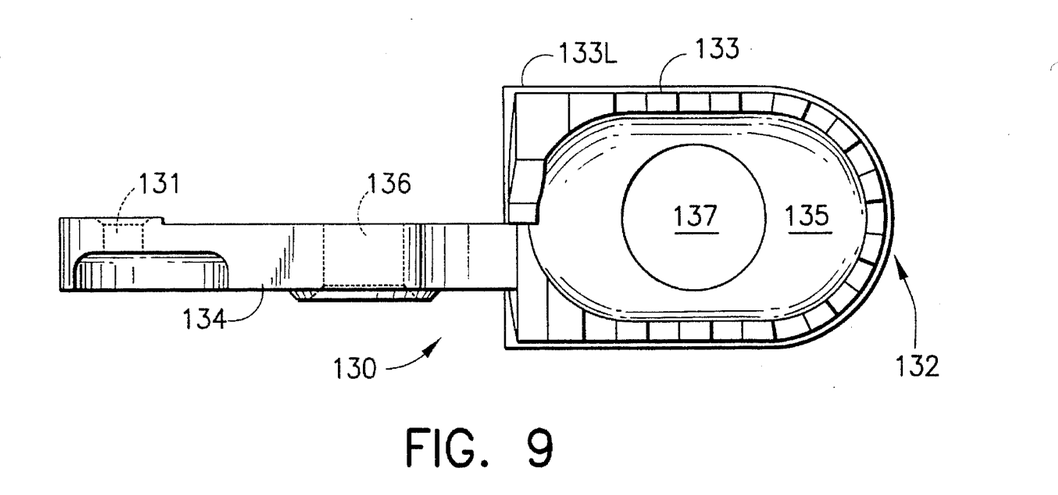
FIG. 9 is a top view of an alternate first embodiment of a biopsy forceps jaw according to the invention.

An alternate first embodiment of the biopsy forceps jaw is shown in FIG. 9. The jaw 130 is substantially the same as the jaw 30 described above, except for the step or lip 133L which extends around outer periphery of the outer edge 133. Such a lip is described in more detail in parent application Ser. No. 08/177,536. The lip 133L may be sharp or dull. In FIG. 9 and the Figures which follow, similar numbers, increased by hundreds, are used to indicate similar features of the different embodiments of the invention.

Figure 10:
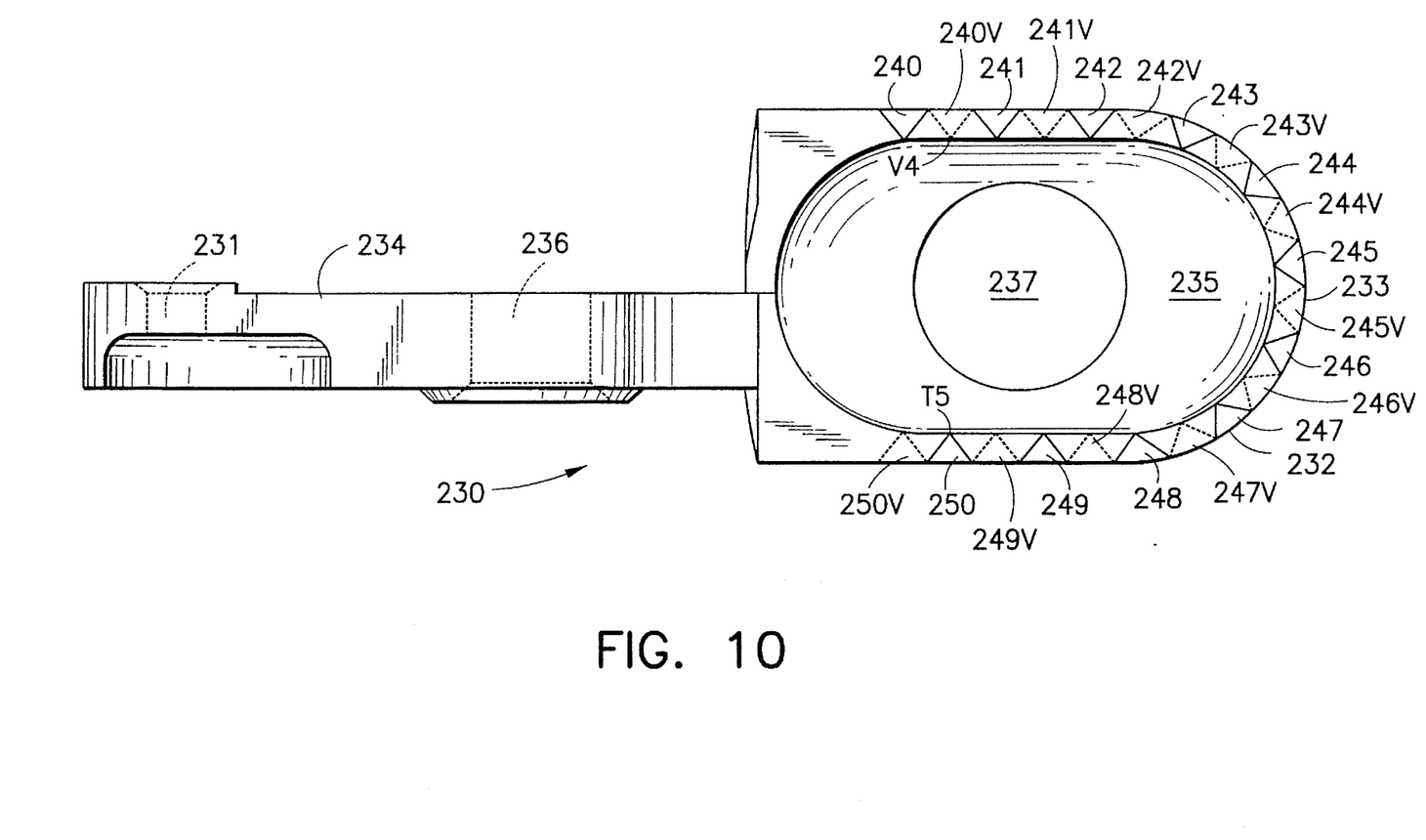
FIG. 10 is a top view of a second embodiment of biopsy forceps jaws according to the invention.
Figure 11:
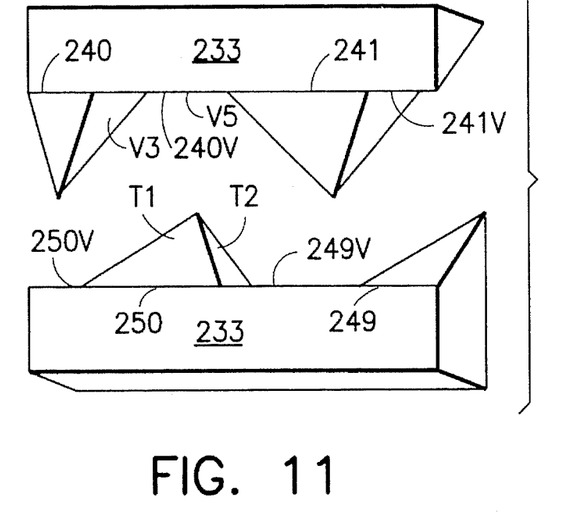
FIG. 11 is a broken perspective view showing the tooth geometry of a pair of biopsy forceps jaws according to the embodiment of FIG. 10 viewed from outside the jaws.
Figure 12:
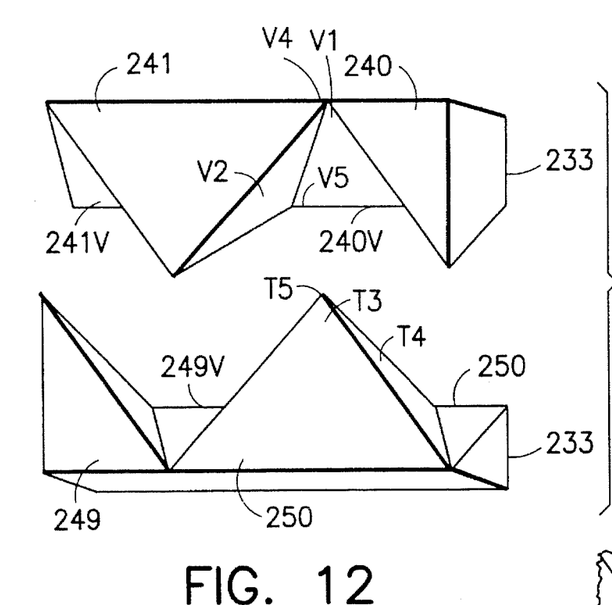
FIG. 12 is a view similar to FIG. 11, but viewed from inside the jaws.

Turning now to FIGS. 10–12, a second embodiment of a biopsy forceps jaw 230 is seen with a distal jaw cup 232, and a proximal tang 234 having a clevis mounting bore 236 and a pull wire coupling bore 231. The overall shape of the distal cup 232 is substantially the same as the jaw cup 32 described above, having an interior hollow 235 with an optional fenestration hole 237. A number of teeth 240–250 are arranged upward and inward from the outer edge 233 of the cup 232 and a number of valleys 240V–250V are interposed between the teeth as seen best in FIG. 10. The primary difference between this embodiment and the first embodiment described above is the geometry of the teeth 240–250. FIGS. 11 and 12 illustrate a broken portion of two jaws 230 spaced apart from each other in their engaging relationship. Here it will be appreciated that each tooth, e.g., tooth 250, is formed as a pyramid having four triangular faces T1–T4 which intersect at a vertex T5. The vertex T5 is located upward and radially inward from the outer edge 233 of the cup 232. Similarly, each valley, e.g., valley 240V, is formed by three triangular surfaces V1–V3 which intersect at a nadir V4. The nadir V4 is located downward and radially inward from the outer edge 233 of the cup 232. It will also be appreciated that two of the surfaces (V2 and V3) of each valley are contiguous with respective T2 and T4 faces of adjacent teeth. The outer edge V5 of each valley appears as a straight line between adjacent teeth, and this edge V5 may be either sharp or dull.

Figure 11A:
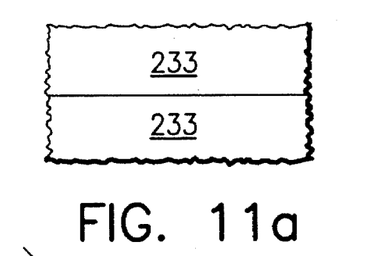
FIG. 11a is a broken perspective view showing the biopsy forceps jaws of FIG. 11 in the closed position viewed from outside the jaws.
Figure 12A:
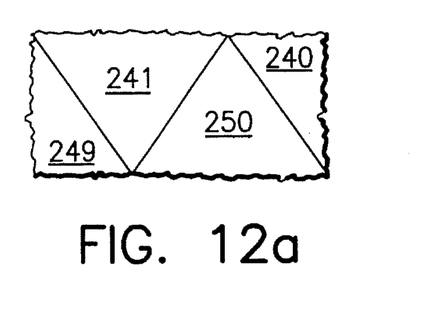
FIG. 12a is a broken perspective view showing the biopsy forceps jaws of FIG. 12 in the closed position viewed from inside the jaws.

The inner face T3 of each tooth is preferably substantially parallel to a plane tangent to the outer edge 233 of the cup, but it will be appreciated that face T3 could be angled either inward or outward relative to the interior of the cup. As seen in FIGS. 11a and 12a, when the jaws are closed, they present a smooth outer surface with a straight line interface between outer edges 233, while from the inside, they present triangular teeth meshed with triangular valleys.

Figure 13:
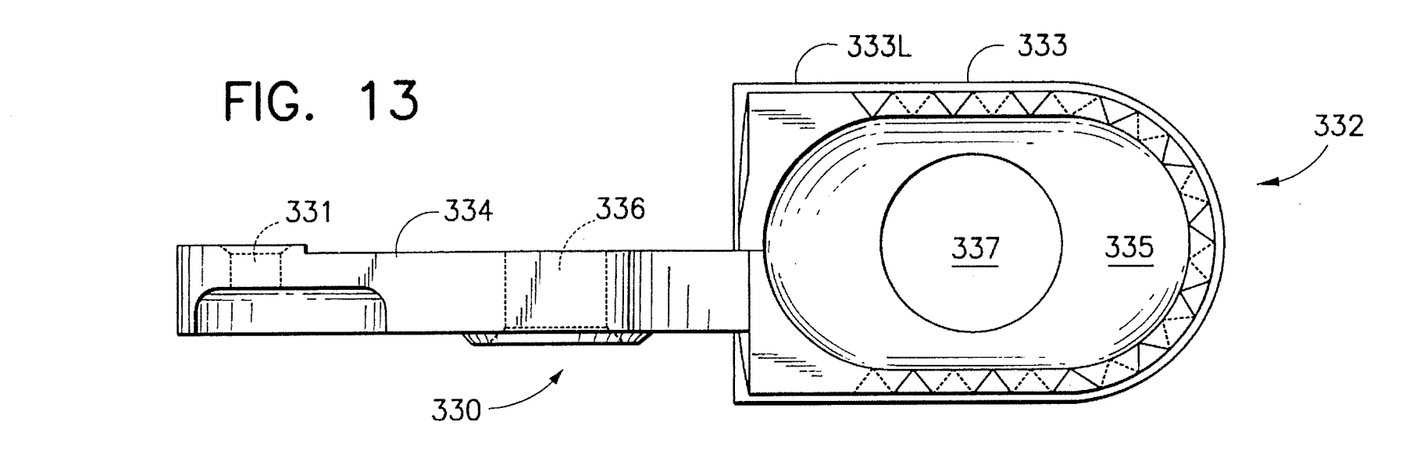
FIG. 13 is a top view of an alternate second embodiment of a biopsy forceps jaw according to the invention.

An alternate second embodiment of the biopsy forceps jaw is shown in FIG. 13. The jaw 330 is substantially the same as the jaw 230 described above, except for the step or lip 333L which extends around outer periphery of the outer edge 333. Such a lip is described in more detail in parent application Ser. No. 08/177,536. The lip 333L may be sharp or dull.

Figure 14:
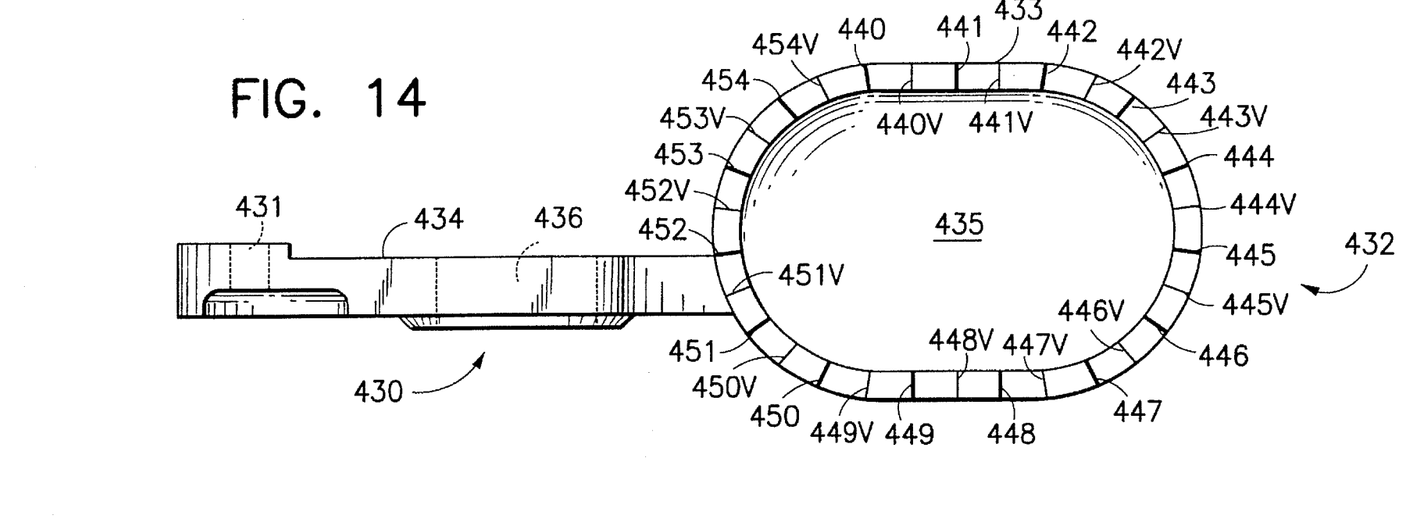
FIG. 14 is a top view of a third embodiment of a biopsy forceps jaw according to the invention.
Figure 15:
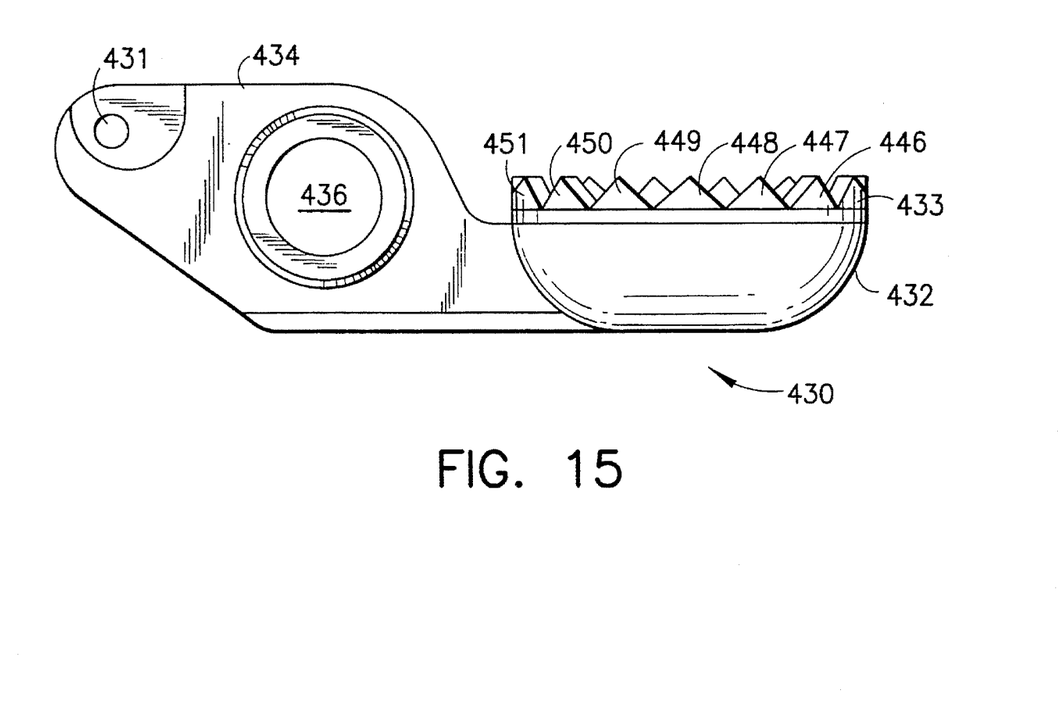
FIG. 15 is a side elevation view of the third embodiment of a biopsy forceps jaw according to the invention.
Figure 16:
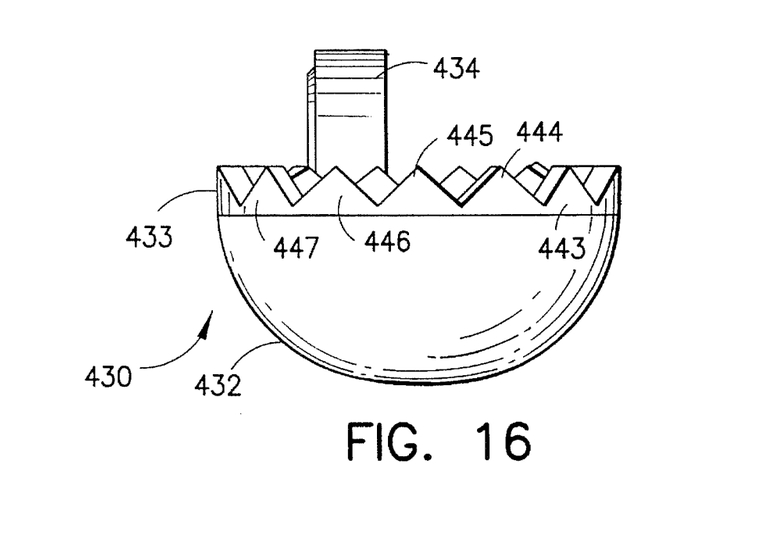
FIG. 16 is an end view of the third embodiment of a biopsy forceps jaw according to the invention.

A third embodiment of the invention is shown in FIGS. 14 through 16. In the third embodiment, the endoscopic biopsy forceps jaw 430 has a distal jaw cup 432 and a proximal tang 434 with a clevis mounting bore 436 and a pull wire coupling bore 431. The overall shape of the distal cup 432 is substantially the same as the jaw cups described above, having an interior hollow 435. In this embodiment however, the outer edge 433 of the cup is not U-shaped, but is an oblate circle as seen best in FIG. 14. A number of teeth 440–454 are arranged along the outer edge 433 of the cup 432 and a number of valleys 440V–454V are interposed between the teeth. In this embodiment of the invention, the teeth 440–454 encircle the entire perimeter of the outer edge. The geometry of the teeth in this embodiment is substantially the same as described in parent application Ser. No. 08/265,217, where the teeth and valleys are formed with two substantially rectangular surfaces which meet at substantially horizontal vertex and nadir lines. The significance of the third embodiment, therefore, is not the specific tooth geometry, but the fact that the teeth are arranged 360° around the cup. As with the other embodiments discussed thus far, at least some of the teeth in this embodiment are arranged radially, and the teeth on either side of the cup are preferably offset by one half pitch so that a pair of mating jaws may be made from a single mold.

Figure 17:
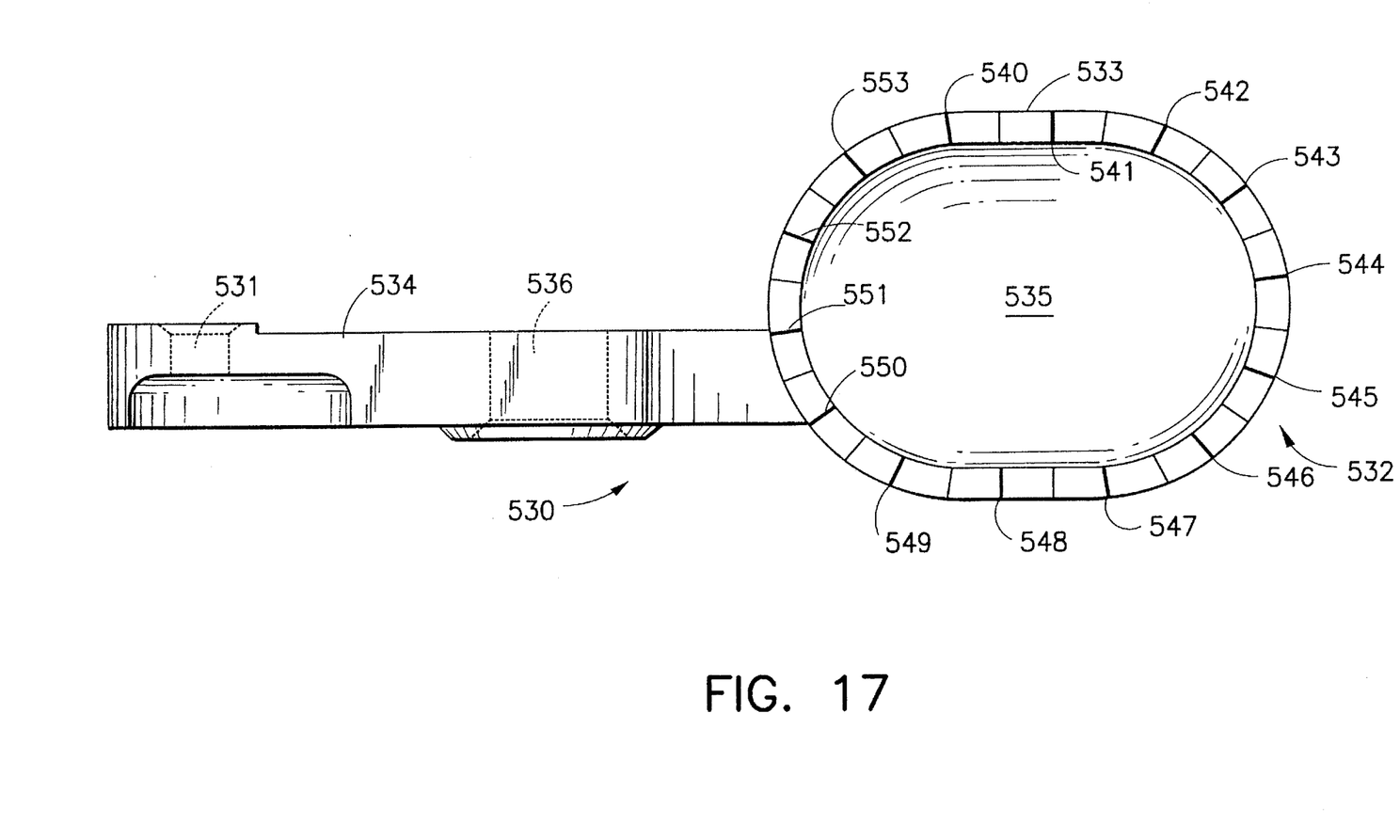
FIG. 17 is a top view of a first alternate third embodiment of the invention.
Figures 18, 19:
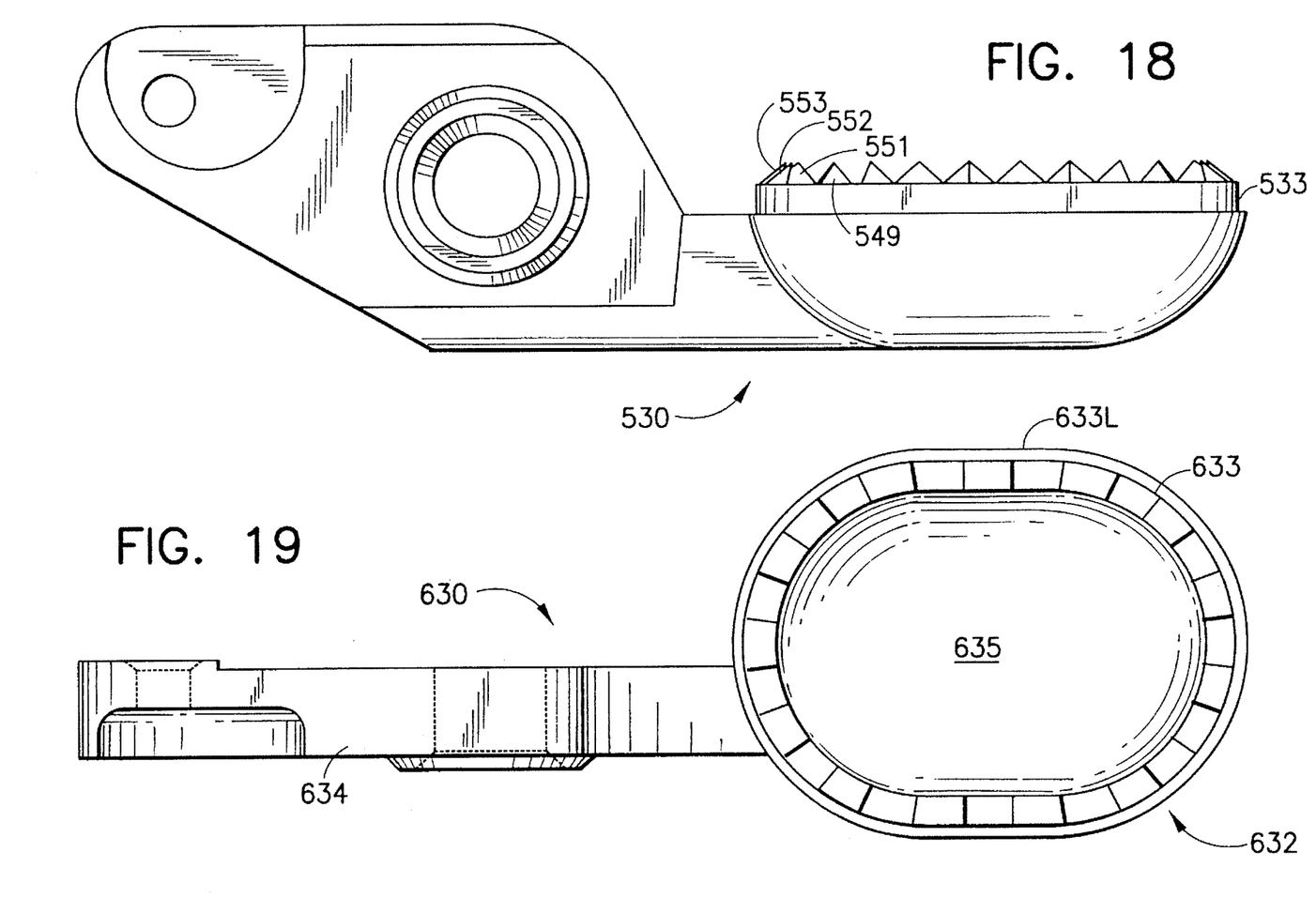
FIG. 18 is a side elevation view of the first alternate third embodiment of the invention.
FIG. 19 is a top view of a second alternate third embodiment of the invention.

A first alternate third embodiment of the invention is shown in FIGS. 17 and 18. The jaw 530 shown in FIGS. 17 and 18 is substantially the same as the jaw 430 described above except that the geometry of the teeth 540–553 is that of the first embodiment of the invention. This embodiment of the invention, therefore, combines features of the oblate circular outer edge of the third embodiment with the tooth geometry of the first embodiment.

A second alternate third embodiment is shown in FIG. 19 and is substantially the same as the embodiment of FIGS. 17 and 18 except for the lip 633L which surrounds the outer edge 633 of the cup 632 of the jaw 630.

Figure 20:
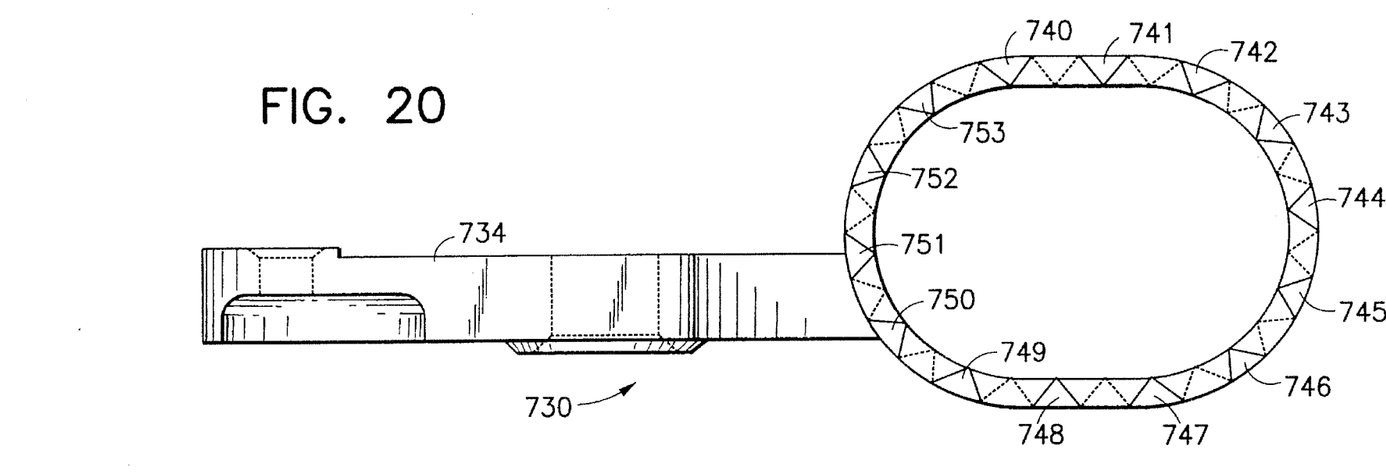
FIG. 20 is a top view of a third alternate third embodiment of the invention.

A third alternate third embodiment of the invention is shown in FIG. 20. The jaw 730 shown in FIG. 20 is substantially the same as the jaw 430 described above except that the geometry of the teeth 740–753 is that of the second embodiment of the invention. This embodiment of the invention, therefore, combines features of the oblate circular outer edge of the third embodiment with the four faced pyramid tooth geometry of the second embodiment.

Figure 21:
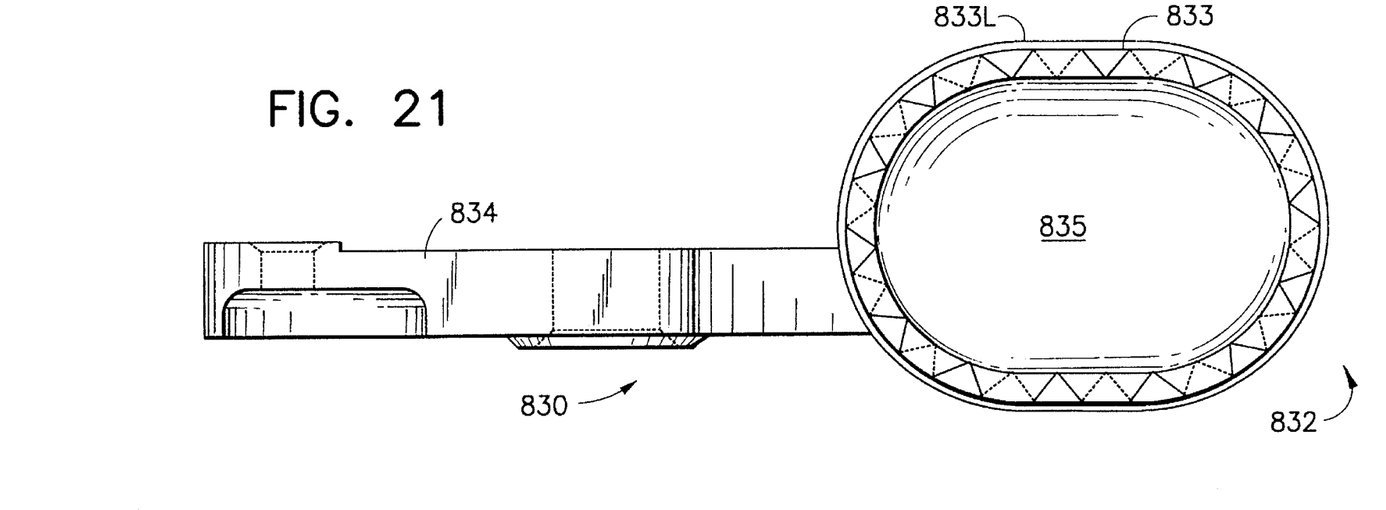
FIG. 21 is a top view of a fourth alternate third embodiment of the invention.

A fourth alternate third embodiment is shown in FIG. 21 and is substantially the same as the embodiment of FIG. 20 except for the lip 833L which surrounds the outer edge 833 of the cup 832 of the jaw 830.

There have been described and illustrated herein several embodiments of an endoscopic biopsy forceps jaw cup.

While particular embodiments of the invention have been described, it is not intended that the invention be limited thereto, as it is intended that the invention be as broad in scope as the art will allow and that the specification be read likewise. Thus, while particular tangs, clevis mounting means, and pull wire coupling means have been disclosed, it will be appreciated that other tangs, clevis mounting means, and pull wire coupling means could be utilized. Also, while specific tooth geometries have been shown to place the peak of each tooth radially inward from the outer edge of the jaw cup, it will be recognized that other tooth geometries could be used with similar results obtained. Moreover, while particular configurations have been disclosed in reference to a biopsy forceps device incorporating the jaws of the invention, it will be appreciated that other configurations could be used as well. Furthermore, while the jaw cups have been disclosed as having teeth which are offset by one half pitch, it will be understood that many of the novel features of the invention can be obtained with nonidentical jaw cups made from two separate molds. It will therefore be appreciated by those skilled in the art that yet other modifications could be made to the provided invention without deviating from its spirit and scope as so claimed.

We claim:

1. An endoscopic biopsy forceps jaw for use with an endoscopic biopsy forceps instrument having a hollow member with a control member extending therethrough, actuating means coupled to the proximal ends of the hollow member and control member for reciprocally moving the control member through the hollow member, and a pair of forceps jaws, at least one of said pair being said endoscopic biopsy forceps jaw, said endoscopic biopsy forceps jaw comprising:

a) a distal jaw cup having an outer edge and an interior hollow portion;

b) a proximal coupling means for coupling said distal jaw cup to at least one of the control member and the hollow member of the biopsy forceps instrument such that the pair of forceps jaws will open and close with the reciprocally moving control member, wherein
   said distal jaw cup has a plurality of teeth extending from said outer edge, each tooth having at least two surfaces which intersect along a line which is angled upward from said outer edge and which terminates at a vertex which is located upward and inward from said outer edge.

2. An endoscopic biopsy forceps jaw according to claim 1, wherein:
   each tooth has a substantially triangular inner surface with said vertex being a vertex of said substantially triangular inner surface, a substantially quadrilateral base, and a surface which extends from said vertex outward and downward to said outer edge.

3. An endoscopic biopsy forceps jaw according to claim 1, wherein:
   said distal jaw cup has a plurality of tooth valleys interposed between said teeth, each tooth valley having a nadir which is located downward and inward from said outer edge.

4. An endoscopic biopsy forceps jaw according to claim 3, wherein:
   each of said tooth valleys has two inclined surfaces which intersect along a line extending inward and downward from said outer edge.

5. An endoscopic biopsy forceps jaw according to claim 1, wherein:
   each of said teeth has four substantially triangular surfaces.

6. An endoscopic biopsy forceps jaw according to claim 3, wherein:
   each of said tooth valleys has three substantially triangular surfaces which intersect at a nadir point located inward and downward from said outer edge.

7. An endoscopic biopsy forceps jaw according to claim 1, wherein:
   said teeth are radially arranged along said outer edge of said distal jaw cup.

8. An endoscopic biopsy forceps jaw according to claim 7, wherein:
   said teeth include first teeth on a first side of said distal jaw cup, and second teeth on a second side of said distal jaw cup, said first teeth and said second teeth being offset by one-half pitch relative to each other.

9. An endoscopic biopsy forceps jaw according to claim 1, wherein:
   said jaw cup is substantially oblate hemispherical.

10. An endoscopic biopsy forceps jaw according to claim 9, wherein:
    said outer edge is substantially U-shaped.

11. An endoscopic biopsy forceps jaw according to claim 9, wherein:
    said outer edge is substantially oblate circular.

12. An endoscopic biopsy forceps jaw according to claim 1, wherein:
    said outer edge has an outer lip, said teeth extending from said outer edge from a location interior of said outer lip.

13. An endoscopic biopsy forceps jaw according to claim 12, wherein:
    said outer lip is unsharpened.

14. An endoscopic biopsy forceps jaw according to claim 12, wherein:
    said outer lip is sharpened.

15. An endoscopic biopsy forceps instrument, comprising:

a) a hollow member having a proximal and a distal end;

b) a control member having a proximal and a distal end and extending through said hollow member;

c) actuating means coupled to said proximal ends of said hollow member and said control member for reciprocally moving said control member through said hollow member; and d) a pair of forceps jaws, wherein
   each of said forceps jaws has a distal jaw cup having an outer edge and an interior hollow portion, a proximal coupling means for coupling said distal jaw cup to at least one of said control member and said hollow member such that the pair of forceps jaws will open and close in response to reciprocally moving said control member, and said distal jaw cup has a plurality of teeth extending from said outer edge, each tooth having at least two surfaces which intersect along a line which is angled upward from said outer edge and which terminates at a vertex which is located upward and inward from said outer edge.

16. An endoscopic biopsy forceps instrument according to claim 15, wherein:
    each tooth has a substantially triangular inner surface with said vertex being a vertex of said substantially triangular inner surface, a substantially quadrilateral base, and a surface which extends from said vertex outward and downward to said outer edge.

17. An endoscopic biopsy forceps instrument according to claim 15, wherein:

said distal jaw cup has a plurality of tooth valleys interposed between said teeth, each tooth valley having a nadir which is located downward and inward from said outer edge.

18. An endoscopic biopsy forceps instrument according to claim 17, wherein:

each of said tooth valleys has two inclined surfaces which intersect along a line extending inward and downward from said outer edge.

19. An endoscopic biopsy forceps instrument according to claim 15, wherein:

each of said teeth has four substantially triangular surfaces.

20. An endoscopic biopsy forceps instrument according to claim 17, wherein:

each of said tooth valleys has three substantially triangular surfaces which intersect at a nadir point located inward and downward from said outer edge.

21. An endoscopic biopsy forceps instrument according to claim 15, wherein:

said teeth are radially arranged along said outer edge of said distal jaw cup.

22. An endoscopic biopsy forceps instrument according to claim 21, wherein:

said teeth include first teeth on a first side of said distal jaw cup, and second teeth on a second side of said distal jaw cup, said first teeth and said second teeth being offset by one half pitch relative to each other.

* * * * *